US009970038B2

(12) United States Patent
Fackler et al.

(10) Patent No.: US 9,970,038 B2
(45) Date of Patent: May 15, 2018

(54) PROCESS FOR THE PRODUCTION OF CARBOHYDRATE CLEAVAGE PRODUCTS FROM A LINGNOCELLULOSIC MATERIAL

(75) Inventors: Karin Fackler, Vienna (AT); Kurt Messner, Vienna (AT); Chularat Krongtaew, Nonthaburi (TH); Ortwin Ertl, Graz (AT)

(73) Assignee: ANNIKKI GMBH, Graz (AT)

( * ) Notice: Subject to any disclaimer, the term of this patent is extended or adjusted under 35 U.S.C. 154(b) by 0 days. days.

(21) Appl. No.: 13/388,725

(22) PCT Filed: Apr. 30, 2010

(86) PCT No.: PCT/AT2010/000138
§ 371 (c)(1),
(2), (4) Date: Mar. 15, 2012

(87) PCT Pub. No.: WO2011/014894
PCT Pub. Date: Feb. 10, 2011

(65) Prior Publication Data
US 2013/0078677 A1  Mar. 28, 2013

(30) Foreign Application Priority Data

Aug. 6, 2009 (AT) ................ A 1252/2009
Sep. 23, 2009 (AT) ................ A 1496/2009
Dec. 23, 2009 (AT) ................ A 2030/2009

(51) Int. Cl.
C12P 19/14 (2006.01)
C12P 7/14 (2006.01)
C12P 7/18 (2006.01)
C12P 7/02 (2006.01)
C12P 5/02 (2006.01)

(52) U.S. Cl.
CPC .......... *C12P 19/14* (2013.01); *C12P 5/023* (2013.01); *C12P 7/02* (2013.01); *C12P 7/14* (2013.01); *C12P 7/18* (2013.01); *Y02E 50/16* (2013.01); *Y02E 50/343* (2013.01)

(58) Field of Classification Search
None
See application file for complete search history.

(56) References Cited

U.S. PATENT DOCUMENTS

| 2004/0163779 A1 | 8/2004 | Pan |
| 2010/0159520 A1 | 6/2010 | Diner et al. |
| 2012/0064574 A1 | 3/2012 | Tokuyasu et al. |
| 2012/0094331 A1 | 4/2012 | Fackler et al. |

FOREIGN PATENT DOCUMENTS

| CA | 2 578 305 A1 | 8/2008 |
| EP | 1 025 305 B1 | 11/2003 |
| EP | 2 017 349 A1 | 1/2009 |
| JP | S62-104586 A | 5/1987 |
| JP | S62-104588 A | 5/1987 |
| JP | 2573107 B2 | 1/1997 |
| JP | 2007-089573 A | 4/2007 |
| JP | 2007-151433 A | 6/2007 |
| JP | 2008-092883 A | 4/2008 |
| JP | 2008-193935 A | 8/2008 |
| JP | 2008-535523 A | 9/2008 |
| JP | 2008-535524 A | 9/2008 |
| JP | 2008-535664 A | 9/2008 |
| JP | 2008-537886 A | 10/2008 |
| WO | 2001/059204 A1 | 8/2001 |
| WO | 2003/093420 A2 | 11/2003 |
| WO | 2006/110891 A2 | 10/2006 |
| WO | 2006/110900 A2 | 10/2006 |
| WO | 2006/110901 A2 | 10/2006 |
| WO | 2006/110902 A1 | 10/2006 |
| WO | WO 2007018442 A2 * | 2/2007 |
| WO | 2008/144903 A1 | 12/2008 |
| WO | 2010/080464 A1 | 7/2010 |
| WO | 2010/124312 A2 | 11/2010 |
| WO | 2010/134455 A1 | 11/2010 |

OTHER PUBLICATIONS

Kaparaju P et al. Bioethanol, biohydrogen, and biogas production from wheat straw in a biorefinery concept. 2009. Bioresource Technology. 100:2562-2568.*
Zhao X et al. Organosolv pretreatment of lignocellulosic biomass for enzymatic hydrolysis. 2009. Applied Microbiology and Biotechnology. 82:815-827.*
Nidetzky B et al. Continuous Enzymatic Production of Xylitol with Simultaneous Coenzyme Regeneration in a Charged Membrane Reactor. 1996. Biotechnology and Bioengineering. vol. 52, pp. 387-396.*
Jeffries, T.W., "Enzymatic removal and utilization of hemicellulose from pulps; paper pulping; xylan saccharification using endo-1, 4-beta-D-xylanase from Aureobasidium pullulans; xylitol and ethanol preparation using Candida shehatae", Database Biotechabs, No. 1991-03990, 1990 [Abstract Only].
Chupka et al., "Oxidation of wood and its components in water-organic media", Proceedings: Seventh International symposium on wood and pulping chemistry, vol. 3, 373-382, China, 1993.
Avgerinos, G.C. & Wang, D.1.C: "Selective Solvent Delignification for Fermentation Enhancement", Biotechnology and Bioengineering. vol. 25, No. 1; 1983, pp. 67-82.
Marton, R: & Granzow, S.: "Ethanol-alkali pulping", TAPPI, vol. 65, No. 6; Jun. 1982; pp. 103-106.
Ivanow T. et al.: "Delignifaction du bois de charme par solvolyse alcaline; cas des solutions ethanol-eau"; La Papeterie 132, 1989, pp. 1-15—English Translation.

(Continued)

Primary Examiner — Paul J Holland
(74) Attorney, Agent, or Firm — Maschoff Brennan

(57) ABSTRACT

A process for the production of carbohydrate cleavage products, characterized by a combination of the measures that a lignocellulosic material is treated with an aqueous solution containing an alcohol, in particular a $C_{1-4}$-alcohol or a phenol, and having a pH-value of between 11.0 and 14.0 in order to cleave lignocellulose and separate cleavage products from the material, whereby a material enriched with cellulose and hemicellulose is obtained, and the obtained material enriched with cellulose and hemicellulose is treated with at least one carbohydrate-cleaving enzyme in order to obtain the carbohydrate cleavage products.

19 Claims, No Drawings

(56) References Cited

OTHER PUBLICATIONS

R.A. Young et al.: "Environmentally Friendly Technologies for the Pulp and Paper Industry"; Wiley Verlag, 1997, ISBN: 978-0-471-1.5770-0, Chapter: Alkaline Organosoly Processes—Abstract Only.
Gould, J.M.: Alkaline Peroxide Delignifcation of Agricultural Residues to Enhance Enzymatic Saceharification; Biotechnology and Bioengineering, vol. 26, No. 1, 1984, pp. 46-52.
JP office action dated Sep. 24, 2014 as received in Application No. 2012-523163 (English translation).
Khimiia drevesiny, 1993, vol. 4, pp. 6-13 (See accompanying statement).
Duncan., "Determination of Furfural", Ind. Eng. Chem. Anal. Ed., vol. 15, Issue 3, 1943, pp. 162-164.
Kline et al., "Volumetric Determination of Pentoses and Pentosans", Bureau of Standards Journal of Research, vol. 8, Issue 1, Research Paper 398 (RP398), pp. 25-35. (1932).
Horwitz et al., "Official Methods of Analysis of the Association of Official Agricultural Chemists", Tenth Edition, Association of Official Agricultural Chemists, 1965, pp. 5.
Polglase., "Polysaccharides Associated With Wood Cellulose", Adv Carbohydr Chem, vol. 10, 1955, pp. 283 and 305.
Smith., "A Study of the Quantitative Formation of Furfural From d-LYXOSE", Massachusetts Institute of Technology, 1939, pp. 1-35.
Avgerinos & Wang, "Selective Solvent Delignification for Fermentation Enhancement", Biotechnology and Bioengineering, vol. 25, Issue 1, Jan. 1983, pp. 67-83.
Polizeli et al., "Xylanases from fungi: properties and industrial applications", Applied Microbiology and Biotechnology, vol. 67, Issue 5, Jun. 2005, pp. 577-591.
JP Office Action dated Oct. 4, 2016 as received in Application No. 2015-254620 (English Translation).
Extended European Search Report dated Nov. 28, 2016 as received in Application No. 16188442.4.

\* cited by examiner

PROCESS FOR THE PRODUCTION OF CARBOHYDRATE CLEAVAGE PRODUCTS FROM A LINGNOCELLULOSIC MATERIAL

The present invention relates to a process for the production of carbohydrate cleavage products, in particular sugars such as pentoses and hexoses, from a lignocellulosic material. Furthermore, the invention relates to a process for obtaining alcohol from the sugars. For the purposes of the present specification and claims, the term "sugar" is intended to encompass also "sugar oligomers".

In connection with the shortage of crude oil and the discussion of corn as an energy supplier, the renewable raw material lignocellulose (straw, wood, waste paper etc.) gains a lot of significance as a starting material for fuels or chemical products. The conversion of lignocellulose may occur in two fundamentally different ways: 1) the "Thermochemical Platform" in which the lignocellulose is first gasified and the synthesis gases are synthesized into desired products, and 2) the "Sugar Platform" in which the main focus lies on utilizing the sugars bound in the polymers cellulose and hemicelluloses, while lignin is still being used predominantly energetically. The present invention can be allocated to the second way.

In contrast to starch, the sugars of lignocellulose are present in tightly cross-linked, polymeric, crystalline structures of the cellulose and the hemicelluloses, which, in addition, are covered with a lignin coat, which thereby leads to an extremely tight complex. The most obvious way of obtaining sugar from lignocellulose would be the direct use of cellulases and hemicellulases. However, this is hampered on the raw material straw or wood by the density of the above-mentioned complex. Due to their high molecular weight, enzymes are unable to penetrate through the narrow pores into the lignocellulose. This means that a first step has to be taken which increases the porosity of the lignocellulose and thereby enables a further enzymatic saccharification.

This first step is referred to as "pretreatment" (decomposition). It is consistently very complex so that, e.g., during the manufacture of "second generation biofuels", up to ⅓ of the production costs have to be spent therefor, which has a negative influence on cost-effectiveness. The methods employed are aimed either at liquefying primarily the hemicelluloses (e.g., steam explosion-, dilute acid-pretreatment) or at achieching the increase in porosity by liquefying lignin (e.g., lime-, ammonia-pretreatment).

For obtaining sugars and their oligomers, respectively, the decomposed lignocellulose substrate can be treated further enzymatically, wherein the type of pretreatment can have a strong influence on enzyme activity and yield. At high reaction temperatures, toxic breakdown products (e.g., furfural) form frequently, which, in case of a directly attached ethanol fermentation, can inhibit the yeasts; see, e.g., Chandra et al., Advances in Biochemical Engineering/Biotechnology, 108:67, 2007; Mansfield et al., Biotechnol. Prog. 15:804, 1999.

A severe disadvantage of these methods is that they are energy-intensive and proceed mainly at temperatures of slightly below 200° C.

A technological improvement in this field, e.g., due to the development of low-temperature methods (i.e., at a temperature of below 100° C.), would mean a decisive progress for any substantial utilization of the raw material lignocellulose. This is the object of the present invention.

From EP 1 025 305 B1, a chemical process for lignin depolymerization (Cu-system) is known. It is based on the catalytic effect of complexed copper in combination with hydrogen peroxide or organic hydroperoxides and is able to oxidatively cleave lignin at temperatures of below 100° C. The complexing agents used in the process are pyridine derivatives. It has been possible to demonstrate on synthetic lignin models that, when $H_2O_2$ is used as an oxidant, a cleavage of ether bonds of the lignin molecule occurs, whereby the lignin polymer disintegrates into oligomeric subunits. Using the Cu-system with an excess of organic hydroperoxides, it is possible to delignify wood. The system based on $H_2O_2$ appears to be better in terms of being technically feasible, has been tested as a bleaching additive in the peroxide bleaching of kraft pulp and has resulted in an improved delignification rate and a higher degree of whiteness.

Furthermore, it is known from "Oxidation of wood and its components in water-organic media", Chupka et al., Proceedings: Seventh International symposium on wood and pulping chemistry, Vol. 3, 373-382, Beijing P.R. China, May 25-28, 1993, that the efficiency of an alkaline catalysis of the oxidation of wood and lignin increases substantially if an organic solvent, e.g., DMSO, acetone, ethanol, is added to the aqueous reaction medium. Furthermore, the authors suggest that, at pH-values of above 11, a drastic increase in the oxidation of the wood and the lignin occurs.

From WO 01/059204, a process for the production of pulp is known in which the starting material is subjected to a pretreatment, wherein the material is treated with a buffer solution and a delignification catalyst (transition metal). Delignification is carried out in the presence of oxygen, hydrogen peroxide or ozone.

In contrast, the process according to the invention for the production of sugars is characterized by a combination of the measures that
- a lignocellulosic material is treated with an aqueous solution containing an alcohol, in particular a $C_{1-4}$-alcohol or a phenol, and having a pH-value of between 11.0 and 14.0 in order to cleave lignocellulose and separate cleavage products from the material, whereby a material enriched with cellulose and hemicellulose is obtained, and
- the obtained material enriched with cellulose and hemicellulose is treated with at least one carbohydrate-cleaving enzyme in order to obtain the carbohydrate cleavage products.

Aliphatic or cycloaliphatic, mono- or polyvalent alcohols or phenols, e.g., $C_{1-6}$-alcohols, in particular a $C_{1-4}$-alcohol such as methanol, ethanol, propanol and butanol, including their isomers; glycols (ethane diols, propane, butane, pentane, hexane diols), glycerol, propenol, butenol, cyclopentanol, cyclohexanol, benzyl alcohol; or phenols such as phenols, cresols, catechols, naphthols, but also amino alcohols such as ethanolamine, methanolamine and hexanolamine are suitable as alcohols. A $C_{1-4}$-alcohol is preferred. For the purposes of the present patent application, phenols are also included in the generic term "alcohol".

Moreover, the alcoholic solution of the lignin extract provides advantageous options for the further reprocessing of the lignin and xylan cleavage products, respectively.

In the process according to the invention, alcohol is present in an aqueous solution preferably in an amount of from 10 to 70% by volume, e.g., from 20 to 50% by volume, preferably from 30 to 40% by volume.

In the process according to the invention, the lignocellulosic material is present in the aqueous solution preferably in a stock density of 3-40% by weight, such as 5-40% by weight, in particular 5-20% by weight.

Preferably, the lignocellulose is cleaved at a temperature of below 100° C., such as below 80° C., e.g., below 60° C.

The pH-value can be adjusted with a base, preferably an inorganic base, for example, a caustic soda solution.

The present invention is based on the realization that a lignocellulosic material treated with an aqueous basic solution containing an alcohol, in particular a $C_{1-4}$-alcohol or a phenol, and having a pH-value of between 11.0 and 14.0 can be processed enzymatically into carbohydrate cleavage products such as sugars in higher yields than a material delignified in another way, in particular without addition of alcohol.

Mainly pentoses and hexoses are formed as carbohydrate cleavage products. Preferred sugars include xylose and glucose.

A preferred embodiment of the process according to the invention is characterized in that the material enriched with cellulose and hemicellulose is treated with a xylanase and a cellulase in order to extract the sugars.

Straw, energy grasses such as, e.g., switch grass, elephant grass or abaca, sisal, bagasse, or untypical lignocellulose substrates such as spelts, e.g., rice spelts, preferably straw, energy grasses, bagasse or spelts, particularly preferably straw or bagasse, e.g., straw, are preferably used as lignocellulosic materials. Straw has a highly hydrophobic surface so that its wetting with aqueous solutions constitutes a problem. It has been shown that, by using alcohol, it is possible to introduce the reaction solution into the pores of the substrate even without pressure and to replace the existing air by reaction solution. Besides, it has been shown that alcohol accelerates the extraction of the cleavage products from straw and contributes to keeping the lignin cleavage products in solution. Furthermore, it has been shown that, in contrast, alcohol reduces the solubility of the hemicellulose and its cleavage products and thus the hemicellulose is kept in the substrate.

By pressing out the liquid phase from the substrate after the decomposition process, the substrate concentration is increased so that smaller enzyme amounts are required for the enzymatic hydrolysis and for other enzymatic subsequent treatments, respectively.

In the production of alcohol, enzyme costs are a critical cost factor. The result of alcohol is that the solubility of the hemicelluloses which possibly have been released during the reaction in the alkaline range in addition to the lignin and of the cleavage products thereof is drastically reduced and that they remain bound to the substrate. The advantages for the process are the high selectivity of the lignin degradation, in the event of a separation of the extraction solution from the solid, a very low concentration of hemicellulose and its cleavage products in the extraction solution, since the hemicellulose remains in the solids content and is thereby maintained for the enzymatic hydrolysis and the extraction of sugar.

Furthermore, the alcoholic solution of the lignin extract provides improved possibilities for the further reprocessing of the lignin and the manufacture of products from lignin.

Furthermore, it has been shown that, by using alcohol, in particular a $C_{1-4}$-alcohol or a phenol, in the alkaline decomposition below 100° C., the degradation of the hemicelluloses is largely prevented so that approximately the entire hemicellulose is available for the further enzymatic cleavage and conversion of the xylose into higher-quality products and is not partially degraded during the decomposition and will not accumulate as a lignin/sugar mixture, such as in other processes.

By the delignification carried out in the decomposition, the porosity of the cell walls of the lignocellulosic material is increased, for example, in case of straw it is increased to such an extent that almost the entire xylose becomes accessible for the xylanase and approximately 100% of the xylan can be hydrolyzed and xylose can be obtained. This renders the process according to the present invention particularly suitable for manufacturing higher-quality products in combination with an enzymatic conversion of the xylose. In doing so, the enzymatic conversion can occur either directly in the mixture of xylose solution and solid, or also with the xylose solution separated from the solid.

In a further alcohol production from the remaining solid, which follows after the enzymatic hydrolysis of the xylan and the conversion according to the invention of xylose into xylitol, enzyme costs are a critical cost factor. They result partly also from unspecific bindings of enzymes to the lignin, see, e.g., Chandra et al, 2007, ibidem. The partial removal of the lignin reduces this loss in activity and has a cost-saving effect.

The advantages for a subsequent enzymatic process are, for example, that a very low concentration of hemicellulose and its cleavage products in the extraction solution results from the high selectivity of the lignin degradation, with the sugar polymers being preserved almost completely, the hemicellulose remains in the solids content and is thereby maintained for the enzymatic hydrolysis and the extraction of sugar as well as its further transformation. The result according to the invention is a maximum material utilization rate and, for example in connection with the use of xylose dehydrogenases, a high cost-effectiveness of the described process.

The implementation of a xylose transformation process into xylitol can be performed after the enzymatic release of the xylose directly in the solid/liquid mixture, which is obtained according to the present process of the invention, which further increases the cost-effectiveness of the entire process.

In the event of a transformation into xylitol, the residual alcohol from the decomposition process, which remains in the substrate after the solid has been pressed out, can be used directly as a substrate for the alcohol dehydrogenase for the regeneration of NAD into NADH. If the process is designed such that, for this purpose, the residual alcohol from the decomposition, which remains in the reaction mixture, is (partially) consumed, a removal of alcohol from the product solution becomes (partially) superfluous and the efficiency of the entire process is thereby further increased.

In the event of a transformation of the lignin cleavage products, the alcohol acts as a radical scavenger and a solvent for cleavage products from an enzymatic, biomimetic or chemical depolymerization of the higher-molecular lignin cleavage products into low-molecular ones.

The small content of hemicelluose and its cleavage products in the extract and the increased solubility of the lignin increase the throughput rates during a separation of the solid from the conversion products as well as their reprocessing by filtration.

The process according to the invention enables, for example, the separation of the three main components of the straw, namely of glucose, xylose as well as lignin, into material flows very low in extraneous materials and their further transformation into higher-quality products such as xylitol, and thus meets the requirements of an ideal biorefinery process.

A further advantage of the process according to the invention in comparison to other decomposition methods which proceed predominantly in a temperature range between 150° C. and 200° C. is its reaction temperature of below 100° C. The small energy expenditure allows to use the lignin obtained during the decomposition as a valuable product, rather than as an energy source for the decomposition method.

After the treatment with the aqueous solution containing an alcohol, in particular a $C_{1-4}$-alcohol or a phenol, and $H_2O_2$, according to the process of the present invention, the solution containing lignin is separated and the decomposed solid is preferably treated with a xylanase, at 30-90° C., e.g., for 6-72 hours, and the liquid phase is separated from the solid, whereupon the liquid phase is preferably reacted further into resultant products, e.g., xylitol.

The solid remaining after the separation of the liquid phase is preferably treated with cellulase, whereby, via a further fermentation of the solid/glucose solution, ethanol, butanol or other fermentation products can be obtained; or the remaining solid is subjected to a thermal or thermochemical conversion and the resulting products such as fuel components, fuel additives and/or other chemical products such as, e.g., phenols are separated; or the remaining solid is subjected to a microbial conversion by bacteria, yeasts or fungi; or the remaining solid is subjected to a further delignification step for the purpose of obtaining a cellulose fibre material.

The remaining solid can be fermented in a biogas plant and can be processed further into biogas.

One of the economically most interesting resultant products of xylose is xylitol.

The main sources for the recovery of xylose are cooking liquors from the pulp industry which contain an abundance of breakdown products, mainly of lignin and of hemicellulose, so that xylose must be obtained by complex separation and purification steps. For example, H. Harms describes in "Willkommen in der natürlichen Welt von Lenzing, weltweit führend in der Cellulosefaser Technologie", Herbsttagung der österreichischen Papierindustrie, Frantschach (Nov. 15, 2007), the recovery of xylose from the thick liquor by gel filtration, a technically very complex method which usually is not used for bulk products. The xylose obtained in this way is then converted catalytically into xylitol.

In a further aspect, the xylose obtained according to the present invention is converted into xylitol without fermentation, by conversion with a xylose reductase, e.g., a xylose dehydrogenase, for example from *Candida tenuis*, wherein optionally a xylose reductase and optionally a cosubstrate for the regeneration of the cofactor and optionally alcohol dehydrogenase and optionally NAD(P)H are added to the xylose solution; in particular with the xylitol obtained being separated from the lignin cleavage products by filtration.

By means of the following Example 1 and Comparative Example 1A, the influence of the pretreatment in the presence of alcohol on the yield of reducing sugars after an enzymatic hydrolysis is documented.

EXAMPLE 1

Pretreatment of Wheat Straw

Wheat straw is crushed to a particle size of approx. 2 cm. 5 g of crushed wheat straw is suspended in a 500 mL reaction vessel in 200 mL of a solution consisting of 49.5% water, 50% ethanol and 0.5% hydrogen peroxide. The suspension is heated to 50° C. in a water bath, is thermostated, and the pH-value of the suspension is adjusted to an initial pH-value of 12 with an aqueous NaOH solution. The mixture is magnetically stirred continuously at 200 rpm, 60° C., for 24 hours. Thereupon, the solids content is filtered off and washed with 1 L of distilled water.

For the enzymatic hydrolysis, 100 mg of a pretreated substrate from each parallel trial were set to pH 4.8 with 9.8 mL of 50 mM Na-acetate buffer and mixed with 200 µL of Accellerase 1000 Suspension (www.genencor.com). Accellerase is an enzyme mixture of cellulases and hemicellulases. The enzymatic hydrolysis was performed at 50° C. in a shaking water bath. The soluble monomers released after 48 hours from hexoses and pentoses were determined in 1 mL of a liquid supernatant in the form of reducing sugars according to the DNS method (Miller et al., Analytical Chemistry 31(3):426, 1959), related to the amount of weighed-in, pretreated substrate and expressed in percent of the maximum theoretical yield.

The maximum theoretical yield of reducing sugars was determined separately and is 705 mg +/–5% per g of untreated straw.

Per test stock, 5 parallel trials were conducted. The yield of reducing sugars was 99%+/–4%.

COMPARATIVE EXAMPLE 1A

Example 1 was repeated, but without the addition of alcohol. The yield of reducing sugars was merely 64%+/–3%.

EXAMPLE 2

Pretreatment of Wheat Straw

Wheat straw is crushed to a particle size of approx. 2 cm. 2.5 g of crushed wheat straw is suspended in a 500 mL reaction vessel in 200 mL of a solution consisting of 49.5% water and 50% isopropanol. The suspension is heated to 50° C. in a water bath, is thermostated, and the pH-value of the suspension is adjusted to an initial pH-value of 13 (or 14, respectively) with an aqueous NaOH solution. The mixture is magnetically stirred continuously at 200 rpm, 60° C., for 24 hours. Thereupon, the solids content is filtered off and washed with 1 L of distilled water.

For the enzymatic hydrolysis, 100 mg of a pretreated substrate from each parallel trial were set to pH 4.8 with 9.8 mL of 50 mM Na-acetate buffer and mixed with 200 µL of Accellerase 1000 Suspension (www.genencor.com). Accellerase is an enzyme mixture of cellulases and hemicellulases. The enzymatic hydrolysis was performed at 50° C. in a shaking water bath. The soluble monomers released after 48 hours from hexoses and pentoses were determined in 1 mL of a liquid supernatant in the form of reducing sugars according to the DNS method, related to the amount of weighed-in, pretreated substrate and expressed in percent of the maximum theoretical yield.

The maximum theoretical yield of reducing sugars was determined separately and is 705 mg +/–5% per g of untreated straw.

Per test stock, 5 parallel trials were conducted. The yield of reducing sugars was 97%+/–4%.

EXAMPLE 3

Enzymatic Xylitol Production from a Xylose Solution Produced from Straw According to the Process Described in Example 2. Isopropanol is Used as a Cosubstrate.

The reaction solution contains 5 mg/mL xylose.

Xylose reductase (XR) from *Candida tenuis* reduces xylose to xylitol. Said XR requires NADH (nicotinamide adenine dinucleotide reduced) as a coenzyme, which is oxidized to the coenzyme $NAD^+$ during the reaction. The regeneration of the oxidized cofactor is effected by the parallel activity of an alcohol dehydrogenase (ADH: enzyme-coupled regeneration). Isopropanol is used as a cosubstrate. Isopropanol and $NAD^+$ are reacted into NADH and acetone by the ADH, as is shown in Reaction Scheme 1:

REACTION SCHEME 1

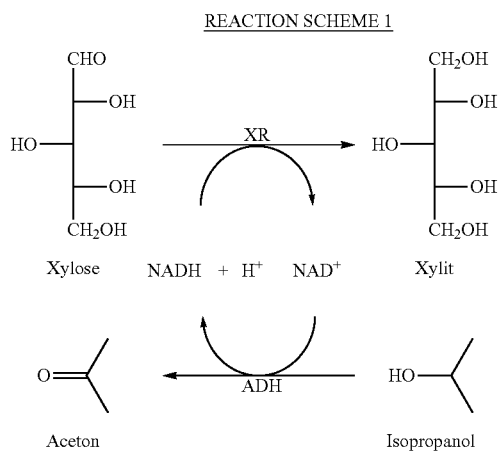

In Table 1, the reaction ratios in the 5 different test reactions #049, #050, #051, #052, #053 and #054 are illustrated:

TABLE 1

| Reaction number | #049 | #050 | #052 | #053 | #054 |
|---|---|---|---|---|---|
| Substrate batch I [µl] | 250 | 250 | 250 | 500 | 500 |
| XR *C. tenuis* 2 U/mL [µL] | | 50 | 50 | | 50 |
| 20 mM NADH [µL] | | 50 | 50 | | 50 |
| ADH *L. kefir* 5 U/mL [µL] | | 50 | 50 | | 50 |
| Isopropanol [µL] | | | 50 | | 50 |
| 50 mM Na-phosphate puffer, pH 7.0 [µL] | 750 | 650 | 550 | 500 | 300 |

Total volume: 1 mL
Temperature: 26 ± 2° C.
Magnetic stirrer: 200 rpm
Time: 15 hours For deactivating the enzymes, all samples were heated to 95° C. for 15 minutes and centrifuged in preparation for the subsequent HPLC analysis.
Analysis-HPLC:
Column SUGAR SP0810+precolumn SUGAR SP-G
Detector: refractive index detector
Eluent: deionized $H_2O$
Flow: 0.75 mL/min
Amount of sample: 10 µL
HPLC quantification precision: ±10%
Retention Time:
Xylose: 13.97 min
Xylitol: 37.73 min
Isopropanol: 16.69 min
Acetone: 16.54 min
Results:
The substrate concentration of sample #049 was determined by HPLC and amounted to 0.9 mg/mL.

The reaction mixture #050 includes only xylose reductase (0.1 U/mL) and NADH (1 mM). After the reaction lasting for 15 hours, 0.085 mg of xylose was consumed. The xylitol concentration was below the detection limit.

Reaction #052 is comparable to Reaction #050, but with the difference that, in this case, the regeneration system is applied. The result is a total conversion of the xylose used. Concentrations used: XR (0.1 U/mL), NADH (1 mM), ADH (0.25 U/mL) and isopropanol (5%).

The xylose concentration of sample #053 was determined to be 2.121 mg/mL, which corresponds to the expected xylose concentration.

Reaction #054 is comparable to Reaction #052, but includes an initial xylose concentration increased by factor 2 (50% substrates in the reaction). The concentration of the xylitol produced was measured to be 0.945 mg xylitol. Concentrations used: XR (0.1 U/mL), NADH (1 mM), ADH (0.25 U/mL) and Isopropanol (5%).

In Table 2, the results of the reactions are summarized based on the measured HPLC data (Xylose consumed and Xylitol recovered; b.D.L. means "below the detection limit"):

TABLE 2

| Reaction number | 049 | 050 | 052 | 053 | 054 |
|---|---|---|---|---|---|
| Xylose prior to the reaction [mg/mL] | 0.9 | 0.815 | 0.8 | 2.121 | 1.945 |
| Xylose after the reaction [mg/mL] | — | 0.815 | b.D.L. | — | 1.013 |
| Xylose consumed in the reaction [mg/mL] | — | b.D.L. | | — | 0.932 |
| Recovery of xylitol [mg/mL] | — | b.D.L. | 0.994 | — | 0.945 |
| Xylitol yield relative to the xylose concentration [%] | — | b.D.L. | 100 | — | 47.9 |

EXAMPLE 4

Enzymatic Xylitol Production from a Xylose Solution Produced from Straw According to the Process Described in Example 2. Ethanol is Used as a Cosubstrate.

The volume of the substrate solution was (cf. Example 2) reduced to 50% using a rotary evaporator in order to increase the xylose concentration (~10 mg/mL xylose).

The regeneration of the oxidized cofactor was effected by the activity of the xylose reductase (XR) from *Candida tenius* which was used and the additional activity of an aldehyde dehydrogenase from *Saccharomyces cerevisiae* which was used (Sigma-Aldrich: Catalogue No. A6338; (EC) No.: 1.2.1.5; CAS No.: 9028-88-0). This is both a substrate-coupled and an enzyme-coupled reaction. Ethanol is used as a cosubstrate. In the first step, ethanol and $NAD^+$ are converted into NADH and acetaldehyde by the activity of the XR. In the second step, acetaldehyde and $NAD^+$ are converted into acetate by the activity of the aldehyde dehydrogenase (AldDH) (cf. for this purpose: Sigma-Aldrich: Catalogue No. A6338; and "Characterization and Potential Roles of Cytosolic and Mitochondrial Aldehyde Dehydrogenases in Ethanol Metabolism in *Saccharomyces cerevisiae*", Wang et al, Molecular Cloning, 1998, Journal of Bacteriology, p. 822-830, respectively). Per mol of converted cosubstrate, 2 mols of reduction equivalent (NADH) would form in this case (cf. Reaction Scheme 2).

REACTION SCHEME 2

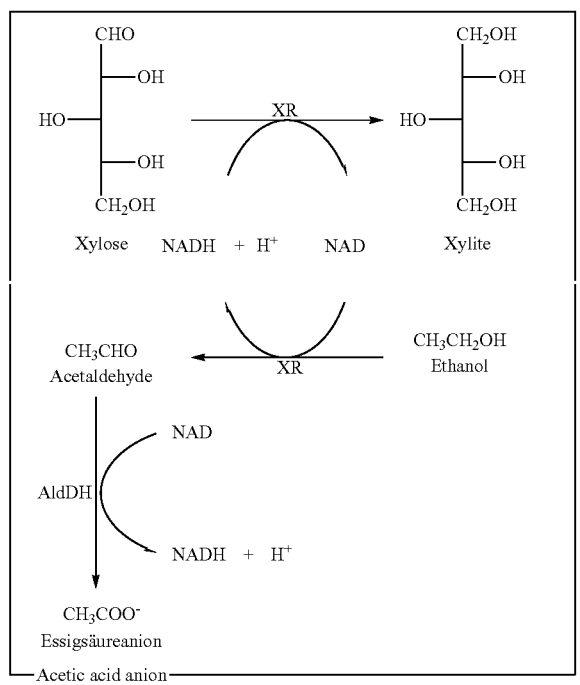

In Table 3, the reaction ratios of the 4 different test reactions 247, 249, 250 and 253 are illustrated. Different ethanol concentrations and AldDH concentrations were used. Cofactor and substrate concentrations were kept constant.

TABLE 3

| Reaction number | 247 | 249 | 250 | 253 |
|---|---|---|---|---|
| Substrate batch III [μL] | 300 (56 mM) | 300 (56 mM) | 300 (56 mM) | 300 (56 mM) |
| XR *C. tenius* 5 U/mL [μL] | 25 (0.25 U/mL) | 25 (0.25 U/mL) | 25 (0.25 U/mL) | 25 (0.25 U/mL) |
| 20 mM NAD+ [μL] | 10 (0.4 mM) | 10 (0.4 mM) | 10 (0.4 mM) | 10 (0.4 mM) |
| AldDH *S. cervisiae* 5 U/mL [μL] | 25 (0.25 U/mL) | 25 (0.25 U/mL) | 0 | 0 |
| Ethanol 50% [μL] | 75 (1286 mM) | 70 (1200 mM) | 75 (1286 mM) | 70 (1200 mM) |
| 50 mM TrisHCl buffer pH 7.0 [μL] | 65 | 70 | 90 | 95 |

Total volume: 0.5 mL
Temperature: 25 ± 2° C.
Thermomixer: 500 rpm
Time 112 hours For deactivating the enzymes, all samples were heated to 70° C. for 15 minutes and centrifuged and filtered in preparation for the subsequent HPLC analysis (PVDF; 0.2 μm).
Analysis-HPLC:
Column SUGAR SP0810+precolumn SUGAR SP-G
Column temperature: 90° C.
Detector: refractive index detector
Eluent: deionized $H_2O$
Flow: 0.90 mL/min
Amount of sample: 10 μL
HPLC quantification precision: ±10%
Results:
The maximum yield (Reaction 249) could be achieved with an ethanol concentration of 1.2 mol/L. In doing so, a total of 1.38 mg/mL of xylitol was produced, which corresponds to a yield of 21.2% of xylitol in theory.

In Table 4, the results of the reactions based on the measured HPLC data are summarized.

TABLE 4

| Reaction number | 247 | 249 | 250 | 253 |
|---|---|---|---|---|
| Theoretical total concentration [mg/mL] | 6.288 | 6.407 | 6.268 | 6.150 |
| Xylose after the reaction [mg/mL] | 5.057 | 5.046 | 5.385 | 5.365 |
| Xylose consumed in the reaction [mg/mL] | 1.231 | 1.361 | 0.883 | 0.785 |
| Recovery of xylitol [mg/mL] | 1.248 | 1.379 | 0.894 | 0.796 |

It is evident from the results that ethanol can be used as a cosubstrate. As can be shown clearly by comparing Reactions 249 (reaction mixture including AldDH) and 253 (reaction mixture without AldDH), the addition of the aldehyde dehydrogenase leads to a clear increase in the yield of xylitol. The difference of converted xylose from xylitol amounts to ~8%. This result in connection with the abovementioned citations from literature allows only the conclusion that AldDH oxidizes the acetaldehyde forming in the first partial reduction further to acetic acid (cf. Reaction Scheme 2). This energetically favourable reaction and the increased concentration of NADH associated therewith shifts the equilibrium from the educt towards the product xylitol in the first partial reaction.

The invention claimed is:

1. A process for the production of xylitol, the process comprising:
   treating a lignocellulosic material with an aqueous solution containing an alcohol and having a pH-value of between 11.0 and 14.0, in order to cleave lignocellulose and separate cleavage products from said lignocellulosic material, whereby a material enriched with cellulose and hemicellulose is obtained, and
   treating said obtained material enriched with cellulose and hemicellulose with a xylanase in order to obtain a xylose solution and solid;
   converting said xylose solution to xylitol by enzymatic conversion without fermentation, wherein NAD(P)H as a cofactor, a cosubstrate for the regeneration of said cofactor, and an alcohol dehydrogenase are added to said xylose.

2. The process of claim 1, wherein said aqueous solution has a pH-value of between 11.0 and 13.0.

3. The process of claim 1, wherein said lignocellulosic material are straw, bagasse, energy grasses and/or spelts.

4. The process of claim 1, wherein said lignocellulosic material is present in said aqueous solution in a stock density of 5-40% by weight.

5. The process of claim 1, wherein said material enriched with cellulose and hemicellulose is converted with a xylanase and a liquid phase obtained is enzymatically converted into xylitol, and a remaining solid:
- is reacted further with cellulase in order to obtain different fermentation products;
or
- is subjected to a thermal or thermochemical conversion;
or
- is subjected to a microbial conversion by bacteria, yeasts, or fungi;
or
- is subjected to a further delignification step for the purpose of obtaining a cellulose fiber material.

6. The process of claim 1, wherein said material enriched with cellulose and hemicellulose is converted with a xylanase and a liquid phase obtained is enzymatically converted into xylitol using a xylose reductase, and a remaining solid:
- is reacted further with cellulase in order to obtain different fermentation products;
or
- is subjected to a thermal or thermochemical conversion;
or
- is subjected to a microbial conversion by bacteria, yeasts, or fungi;
or
- is subjected to a further delignification step for the purpose of obtaining a cellulose fiber material.

7. The process of claim 5, wherein said remaining solid is fermented in a biogas plant and is processed further into biogas.

8. The process of claim 1, wherein said alcohol includes a $C_{1-4}$-alcohol or a phenol.

9. The process of claim 8, wherein said lignocellulosic material are straw, bagasse, energy grasses and/or spelts.

10. The process of claim 9, wherein said lignocellulosic material is present in said aqueous solution in a stock density of 5-40% by weight.

11. The process of claim 6, wherein said remaining solid is fermented in a biogas plant and is processed further into biogas.

12. The process of claim 1, wherein said cleavage occurs at a temperature below 100° C.

13. The process of claim 1, wherein glucose, xylose and lignin components of said lignocellulosic material are obtained in separated material flows.

14. The process of claim 1, wherein said enzymatic conversion from xylose to xylitol is performed directly in a mixture of said xylose solution and said solid.

15. The process of claim 1, wherein after treating said lignocellulosic material with said aqueous solution containing said alcohol, a solution containing lignin is separated and a decomposed solid remaining after said separation is treated with a xylanase, and a liquid phase is separated from said decomposed solid.

16. The process of claim 1, wherein treatment with said xylanase is conducted at 30-90° C.

17. The process of claim 1, wherein said alcohol is at a concentration from 30% to 70% by volume in said aqueous solution so as to be sufficient to reduce solubility of hemicellulose and retain said hemicellulose in said lignocellulosic material so as to reduce loss of hemicellulose from said lignocellulosic material.

18. The process of claim 1, wherein said treating of said lignocellulosic material is performed without hydrogen peroxide.

19. The process of claim 1, wherein said cosubstrate for regeneration of said cofactor is selected from the group consisting of ethanol and isopropanol.

* * * * *